(12) United States Patent
Varkhedkar et al.

(10) Patent No.: US 6,451,798 B2
(45) Date of Patent: Sep. 17, 2002

(54) SUBSTITUTED ALKYL PIPERAZINE DERIVATIVES

(75) Inventors: Vaibhav Varkhedkar, Sunnyvale; Venkata P. Palle; Jeff Zablocki, both of Mountain View; Elfatih Elzein, Fremont; Brent K. Blackburn, Los Altos, all of CA (US)

(73) Assignee: CV Therapeutics, Inc., Palo Alto, CA (US)

( * ) Notice: Subject to any disclaimer, the term of this patent is extended or adjusted under 35 U.S.C. 154(b) by 0 days.

(21) Appl. No.: 09/792,167

(22) Filed: Feb. 22, 2001

Related U.S. Application Data

(60) Provisional application No. 60/209,262, filed on Jun. 5, 2000, and provisional application No. 60/184,306, filed on Feb. 22, 2000.

(51) Int. Cl.[7] ............... A61K 31/495; C07D 295/15; C07D 241/08
(52) U.S. Cl. ............... 514/252.12; 544/400
(58) Field of Search ............ 544/400; 514/252.12

(56) References Cited

U.S. PATENT DOCUMENTS

| | | | |
|---|---|---|---|
| 3,710,795 A | | 1/1973 | Higuchi et al. |
| 4,567,264 A | * | 1/1986 | Kluge et al. ............ 544/400 |
| 5,472,707 A | | 12/1995 | Samuels et al. |
| 5,506,229 A | * | 4/1996 | Dow et al. ............ 514/255 |
| 5,670,171 A | | 9/1997 | Santus et al. |
| 5,906,988 A | | 5/1999 | Dow |

FOREIGN PATENT DOCUMENTS

| | | |
|---|---|---|
| CA | 2054544 | 5/1992 |
| EP | 0 068 544 | 1/1983 |
| EP | 0 143 016 | 5/1985 |
| EP | 0 407 780 | 1/1991 |
| EP | 0 483 932 | 6/1992 |
| JP | 03 141258 A | 6/1991 |

OTHER PUBLICATIONS

Pepine et al., "A Controlled Trial with a Novel Anti–Ischemic Agent, Ranolazine, in Chronic Stable Angina Pectoris That is Responsive to Coventional Antianginal Agents", *American Journal of Cardiology*, vol. 84, pp. 46–50 (1999).

* cited by examiner

*Primary Examiner*—Emily Bernhardt
(74) *Attorney, Agent, or Firm*—McDonnell Boehnen Hulbert & Berghoff

(57) ABSTRACT

Novel compounds of the general formula:

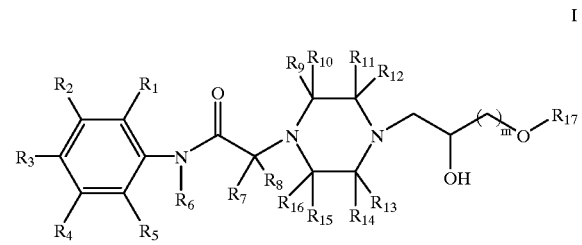

I and pharmaceutically acceptable acid addition salts thereof, wherein the compounds are useful in therapy to protect skeletal muscles against damage resulting from trauma or to protect skeletal muscles subsequent to muscle or systemic diseases such as intermittent claudication, to treat shock conditions, to preserve donor tissue and organs used in transplants, in the treatment of cardiovascular diseases including atrial and ventricular arrhythmias, Prinzmetal's (variant) angina, stable angina, and exercise induced angina, congestive heart disease, and myocardial infarction.

26 Claims, No Drawings

SUBSTITUTED ALKYL PIPERAZINE DERIVATIVES

This application claims priority of U.S. Patent Application 60/184,306 filed on Feb. 22, 2000, and to U.S. Patent Application 60/209,262 filed on Jun. 5, 2000, the specifications of each of which are incorporated herein by reference.

BACKGROUND OF THE INVENTION

1. Field of the Invention

The present invention is concerned with substituted piperazine compounds, therapeutic dosage forms including one or more of the compounds, and methods for treating diseases in mammals, and in particular, in a human in a therapy selected from the group including protecting skeletal muscles against damage resulting from trauma, protecting skeletal muscles subsequent to muscle or systemic diseases such as intermittent claudication, to treat shock conditions, to preserve donor tissue and organs used in transplants, and to treat cardiovascular diseases including atrial and ventricular arrhythmias, Prinzmetal's (variant) angina, stable angina, and exercise induced angina, congestive heart disease, and myocardial infarction.

2. Description of the Art

U.S. Pat. No. 4,567,264, the specification of which is incorporated herein by reference, discloses a class of substituted piperazine compounds that includes a compound known as ranolazine, (±)-N-(2,6-dimethylphenyl)-4-[2-hydroxy-3-(2-methoxyphenoxy)propyl]-1-piperazineacetamide, and its pharmaceutically acceptable salts, and their use in the treatment of cardiovascular diseases, including arrhythmias, variant and exercise-induced angina, and myocardial infarction.

U.S. Pat. No. 5,506,229, which is incorporated herein by reference, discloses the use of ranolazine and its pharmaceutically acceptable salts and esters for the treatment of tissues experiencing a physical or chemical insult, including cardioplegia, hypoxic or reperfusion injury to cardiac or skeletal muscle or brain tissue, and for use in transplants. In particular, ranolazine is particularly useful for treating arrhythmias, variant and exercise-induced angina, and myocardial infarction by partially inhibiting cardiac fatty acid oxidation. Conventional oral and parenteral ranolazine formulations are disclosed, including controlled release formulations. In particular, Example 7D of U.S. Pat. No. 5,506,229 describes a controlled release formulation in capsule form comprising microspheres of ranolazine and microcrystalline cellulose coated with release controlling polymers.

Despite the important discovery that ranolazine is a very useful cardiac therapeutic agent, there remains a need for compounds that are partial fatty acid oxidation inhibitors that have a half-life greater than ranolazine and that have activities as least similar to ranolazine.

SUMMARY OF THE INVENTION

This invention includes novel substituted piperazine compounds that are partial fatty acid oxidation inhibitors with good therapeutic half-lives.

This invention also includes novel substituted piperazine compounds that can be administered to a mammal to protect skeletal muscles against damage resulting from trauma, to protecting skeletal muscles subsequent to muscle or systemic diseases such as intermittent claudication, to treat shock conditions, to preserve donor tissue and organs used in transplants, and to treat cardiovascular diseases including atrial and ventricular arrhythmias, Prinzmetal's (variant) angina, stable angina, and exercise induced angina, congestive heart disease, and myocardial infarction.

This invention includes a class of substituted piperazine compounds having the following formula:

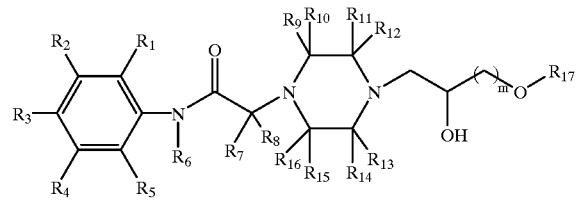

I wherein
m=1, 2, or 3;

$R^1$, $R^2$, $R^3$, $R^4$ and $R^5$ are each independently selected from the group consisting of hydrogen, halo, $NO_2$, $CF_3$, CN, $OR^{20}$, $SR^{20}$, $N(R^{20})_2$, $S(O)R^{22}$, $SO_2R^{22}$, $SO_2N(R^{20})_2$, $NR^{20}CO_2R^{22}$, $NR^{20}CON(R^{20})_2$, $COR^{20}$, $CO_2R^{20}$, $CON(R^{20})_2$, $NR^{20}SO_2R^{22}$, $C_{1-15}$ alkyl, $C_{2-15}$ alkenyl, $C_{2-15}$ alkynyl, heterocyclyl, aryl, and heteroaryl, wherein the alkyl and aryl substituent are optionally substituted with 1 substituent selected from the group consisting of halo, $NO_2$, $CF_3$, CN, $OR^{20}$, $SR^{20}$, $N(R^{20})_2$, $S(O)R^{22}$, and $SO_2R^{22}$;

$R^6$, $R^7$ and $R^8$ each independently selected from the group consisting of hydrogen or $C_{1-3}$ alkyl;

$R^9$, $R^{10}$, $R^{11}$, $R^{12}$, $R^{13}$, $R^{14}$, $R^{15}$ and $R^{16}$ are each independently selected from the group consisting of hydrogen, $CO_2R^{20}$, $CON(R^{20})_2$, $C_{1-4}$ alkyl, or aryl wherein the alkyl and aryl substituents are optionally substituted with 1 substituent selected from the group consisting of halo, $CF_3$, CN, $OR^{20}$, $N(R^{20})_2$, $CO_2R^{20}$, $CON(R^{20})_2$ or aryl, wherein $R^9$ and $R^{10}$ may together form a carbonyl, or $R^{11}$ and $R^{12}$ may together form a carbonyl, or $R^{13}$ and $R^{14}$ may together form a carbonyl, or $R^{15}$ and $R^{16}$ may together form a carbonyl with the proviso that $R^{11}$ and $R^{13}$ or $R^9$ and $R^{15}$ or $R^9$ and $R^{11}$ or $R^{11}$ and $R^{15}$ or $R^9$ and $R^{13}$ may join together to form a ring including from 1 to 3 carbon atoms;

$R^{17}$ is selected from the group consisting of alkyl, cycloalkyl, and fused phenylcycloalkyl wherein the point of attachment is on the cycloalkyl wherein the alkyl, cycloalkyl, and fused phenylcycloalkyl are optionally substituted with from 1 to three substituents selected from the group consisting of halo, $CF_3$, CN, $OR^{20}$, $SR^{20}$, $S(O)R^{22}$, $SO_2R^{22}$, $SO_2N(R^{20})_2$, $NR^{20}CO_2R^{22}$, $C_{1-2}$ alkyl, and aryl wherein the optional aryl substituent is optionally substituted with from 1 to 3 substituents selected from the group consisting of halo, phenyl, $CF_3$, CN, $OR^{20}$, and $C_{1-6}$ alkyl;

$R^{20}$ is selected from the group consisting of H, $C_{1-15}$ alkyl, aryl, or heteroaryl, wherein the alkyl and aryl substituents are optionally substituted with 1 substituent selected from the group consisting of halo, alkyl, mono- or dialkylamino, alkyl, CN, —O—$C_{1-6}$ alkyl, or $CF_3$; and $R^{22}$ is selected from the group consisting of $C_{1-15}$ alkyl, aryl, or heteroaryl, wherein the alkyl and aryl substituents are optionally substituted with 1 substituent selected from the group consisting of halo, alkyl, monoalkylamino, dialkylamino, alkyl amide, aryl amide, heteroaryl amide, CN, O—$C_{1-6}$ alkyl, $CF_3$, or heteroaryl.

In still another embodiment, this invention is a substituted piperazine compound selected from the group consisting of 2-({2-[4-(3-isopropoxy-2-hydroxypropyl)piperazinyl]-N-({2,6-dimethylphenyl)acetamide; N-(2,6-dimethylphenyl)-

2-[4-(2-hydroxy-3-indan-2-yloxypropyl)piperazinyl] acetamide; N-(2,6-dimethylphenyl)-2-{4-[2-hydroxy-3-(phenylmethoxy)propyl]piperazinyl}acetamide, 2-({2-[4-(3-cyclopentyloxy-2-hydroxypropyl)piperazinyl]-N-({2,6-dimethylphenyl)acetamide, 2-({2-[4-(3-cyclohexyloxy-2-hydroxypropyl)piperazinyl]-N-({2,6-dimethylphenyl)acetamide, 2-[4-(3-{[4-(tert-butyl)phenyl]methoxy}-2-hydroxypropyl)piperazinyl]-N-(2,6-dimethylphenyl)acetamide, N-(2,6-dimethylphenyl)-2-(4-{3-[(2-fluorophenyl)methoxy]-2-hydroxypropyl}piperazinyl)acetamide, 2-(4-{3-[(2,4-difluorophenyl)methoxy]-2-hydroxypropyl}piperazinyl)-N-(2,6-dimethylphenyl)acetamide, N-(2,6-dimethylphenyl)-2-[4-(2-hydroxy-3-{[4-(trifluoromethyl)phenyl]methoxy}propyl)piperazinyl]acetamide, N-(2,6-dimethylphenyl)-2-(4-{2-hydroxy-3-[(2-methoxyphenyl)methoxy]propyl}piperazinyl)acetamide, 2-(4-{3-[(2,4-dimethoxyphenyl)methoxy]-2-hydroxypropyl}piperazinyl)-N-(2,6-dimethylphenyl)acetamide, N-(2,6-dimethylphenyl)-2-(4-{2-hydroxy-3-[(4-methoxyphenyl)methoxy]propyl}piperazinyl)acetamide, N-(2,6-dimethylphenyl)-2-(4-{3-[(4-fluorophenyl)methoxy]-2-hydroxypropyl}piperazinyl)acetamide, N-(2,6-dimethylphenyl)-2-(4-{2-hydroxy-3-[(4-methylphenyl)methoxy]propyl}piperazinyl)acetamide, N-(2,6-dimethylphenyl)-2-(4-{2-hydroxy-3-[(4-phenylphenyl)methoxy]propyl}piperazinyl)acetamide, N-(2,6-dimethylphenyl)-2-(4-{3-[(4-butylphenyl)methoxy]-2-hydroxypropyl}piperazinyl)acetamide, N-(2,6-dimethylphenyl)-2-{4-[2-hydoxy-3-(2-naphthylmethoxy)propyl]piperazinyl}acetamide, N-(2,6-dimethylphenyl)-2-{4-[3-(cyclohexylmethoxy)-2-hydroxypropyl]piperazinyl}acetamide, and N-(2,6-dimethylphenyl)-2-(4-{3-[(4-fluorophenyl)methoxy]-2-hydroxypropyl}-3,3-dimethylpiperazinyl)acetamide.

In yet another embodiment, this invention is a method for administering one or more composition of this invention to a mammal in a treatment selected from the group consisting of protecting skeletal muscles against damage resulting from trauma, protecting skeletal muscles subsequent to muscle or systemic diseases such as intermittent claudication, to treat shock conditions, to preserve donor tissue and organs used in transplants, and to treat cardiovascular diseases including atrial and ventricular arrhythmias, Prinzmetal's (variant) angina, stable angina, and exercise induced angina, congestive heart disease, and myocardial infarction.

DETAILED DESCRIPTION OF THE INVENTION

This invention concerns substituted piperazine compounds having the following formula:

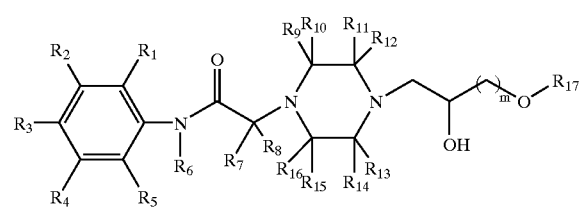

I wherein $m$=1, 2, or 3;

$R^1$, $R^2$, $R^3$, $R^4$ and $R^5$ are each independently selected from the group consisting of hydrogen, halo, $NO_2$, $CF_3$, CN, $OR^{20}$, $SR^{20}$, $N(R^{20})_2$, $S(O)R^{22}$, $SO_2R^{22}$, $SO_2N(R^{20})_2$, $NR^{20}CO_2R^{22}$, $NR^{20}CON(R^{20})_2$, $COR^{20}$, $CO_2R^{20}$, CON$(R^{20})_2$, $NR^{20}SO_2R^{22}$, $C_{1-15}$ alkyl, $C_{2-15}$ alkenyl, $C_{2-15}$ alkynyl, heterocyclyl, aryl, and heteroaryl, wherein the alkyl and aryl substituent are optionally substituted with 1 substituent selected from the group consisting of halo, $NO_2$, $CF_3$, CN, $OR^{20}$, $SR^{20}$, $N(R^{20})_2$, $S(O)R^{22}$, and $SO_2R^{22}$;

$R^6$, $R^7$ and $R^8$ each independently selected from the group consisting of hydrogen or $C_{1-3}$ alkyl;

$R^9$, $R^{10}$, $R^{11}$, $R^{12}$, $R^{13}$, $R^{14}$, $R^{15}$ and $R^{16}$ are each independently selected from the group consisting of hydrogen, $CO_2R^{20}$, $CON(R^{20})_2$, $C_{1-4}$ alkyl, or aryl wherein the alkyl and aryl substituents are optionally substituted with 1 substituent selected from the group consisting of halo, $CF_3$, CN, $OR^{20}$, $N(R^{20})_2$, $CO_2R^{20}$, $CON(R^{20})_2$ or aryl, wherein $R^9$ and $R^{10}$ may together form a carbonyl, or $R^{11}$ and $R^{12}$ may together form a carbonyl, or $R^{13}$ and $R^{14}$ may together form a carbonyl, or $R^{15}$ and $R^{16}$ may together form a carbonyl with the proviso that $R^{11}$ and $R^{13}$ or $R^9$ and $R^{15}$ or $R^9$ and $R^{11}$ or $R^{11}$ and $R^{15}$ or $R^9$ and $R^{13}$ may join together to form a ring including from 1 to 3 carbon atoms;

$R^{17}$ is selected from the group consisting of alkyl, cycloalkyl, and fused phenylcycloalkyl wherein the point of attachment is on the cycloalkyl wherein the alkyl, cycloalkyl, and fused phenylcycloalkyl are optionally substituted with from 1 to three substituents selected from the group consisting of halo, $CF_3$, CN, $OR^{20}$, $SR^{20}$, $S(O)R^{22}$, $SO_2R^{22}$, $SO_2N(R^{20})_2$, $NR^{20}CO_2R^{22}$, $C_{1-2}$ alkyl, and aryl wherein the optional aryl substituent is optionally substituted with from 1 to 3 substituents selected from the group consisting of halo, phenyl, $CF_3$, CN, $OR^{20}$, and $C_{1-6}$ alkyl;

$R^{20}$ is selected from the group consisting of H, $C_{1-15}$ alkyl, aryl, or heteroaryl, wherein the alkyl and aryl substituents are optionally substituted with 1 substituent selected from the group consisting of halo, alkyl, mono- or dialkylamino, alkyl, CN, —O—$C_{1-6}$ alkyl, or $CF_3$; and $R^{22}$ is selected from the group consisting of $C_{1-15}$ alkyl, aryl, or heteroaryl, wherein the alkyl and aryl substituents are optionally substituted with 1 substituent selected from the group consisting of halo, alkyl, monoalkylamino, dialkylamino, alkyl amide, aryl amide, heteroaryl amide, CN, O—$C_{1-6}$ alkyl, $CF_3$, or heteroaryl.

It is preferred that m=1 or 2 and most preferred when m=1.

In preferred compositions of this invention, $R^1$, $R^2$, $R^3$, $R^4$ and $R^5$ are each independently selected from the group consisting of hydrogen, halo, $CF_3$, $OR^{22}$ and $C_{1-4}$ alkyl and wherein $R^{22}$ is a $C_{1-3}$ alkyl. In other preferred compositions, $R^1$, $R^2$, $R^3$, $R^4$ and $R^5$ are each independently selected from the group consisting of hydrogen, $CF_3$, $OR^{20}$, or $C_{1-2}$ alkyl. More preferably $R^1$, $R^2$, $R^3$, $R^4$ and $R^5$ are each independently selected from the group consisting of hydrogen, or methyl with $R^2$, $R^3$, and $R^4$ as hydrogen and $R^1$ and $R^5$ as methyl being preferred.

In other preferred compositions of this invention, $R^6$, $R^7$ and $R^8$ each independently selected from the group consisting of hydrogen and $C_{1-3}$ alkyl with hydrogen or methyl being preferred and hydrogen being most preferred.

In yet other preferred compositions of this invention, $R^9$, $R^{10}$, $R^{11}$, $R^{12}$, $R^{13}$, $R^{14}$, $R^{15}$ and $R^{16}$ are each independently selected from the group consisting of hydrogen, $CON(R^{20})_2$, $C_{1-4}$ alkyl, or aryl wherein the alkyl and aryl substituents are each optionally substituted with 1 substituent selected from the group consisting of halo, $CF_3$, $OR^{20}$, $N(R^{20})_2$, CON$(R^{20})_2$ or aryl wherein $R^9$ and $R^{10}$ may together form a carbonyl, or $R^{11}$ and $R^{12}$ may together form a carbonyl, or $R^{13}$ and $R^{14}$ may together form a carbonyl, or $R^{15}$ and $R^{16}$ may together form a carbonyl with the proviso that $R^{11}$ and $R^{13}$ or $R^9$ and $R^{15}$ or $R^9$ and $R^{11}$ or $R^{11}$ and $R^{15}$ or $R^9$ and $R^{13}$ may join together to form a ring. In alternative preferred compositions, $R^9$, $R^{10}$, $R^{11}$, $R^{12}$, $R^{13}$, $R^{14}$, $R^{15}$ and $R^{16}$ are each independently selected from the group consisting of hydrogen and $C_{1-4}$ alkyl, or $R^9$ and $R^{10}$ together form a carbonyl, or $R^{11}$ and $R^{12}$ together form a carbonyl, or $R^{13}$ and $R^{14}$ together form a carbonyl, or $R^{15}$ and $R^{16}$ together form a carbonyl, $R^{10}$ and $R^{11}$ together form —$CH_2CH_2CH_2CH_2$—. In another embodiment, $R^9$, $R^{10}$, $R^{11}$, $R^{12}$, $R^{13}$, $R^{14}$, $R^{15}$ and $R^{16}$ are each independently selected from the group consisting of hydrogen, or $C_{1-2}$ alkyl, wherein the alkyl substituent is optionally substituted with 1 substituent selected from the group consisting of $N(R^{20})_2$, or aryl or wherein $R^9$ and $R^{10}$ may together form a carbonyl. More preferably, $R^9$, $R^{10}$, $R^{11}$, $R^{12}$, $R^{13}$, $R^{14}$, $R^{15}$ and $R^{16}$ are each independently selected from the group consisting of hydrogen or $C_{1-2}$ alkyl, or wherein $R^9$ and $R^{10}$ may together form a carbonyl. In another embodiment, $R^{11}$ and $R^{15}$ are each selected from the group consisting of hydrogen or methyl, $R^9$, $R^{10}$, $R^{12}$, $R^{13}$, $R^{14}$ and $R^{16}$ are each hydrogen and $R^9$ and $R^{10}$ may together form a carbonyl, or, $R^9$, $R^{10}$, $R^{11}$, $R^{12}$, $R^{13}$, $R^{14}$, $R^{15}$ and $R^{16}$ may each be hydrogen.

In compounds of this invention, $R^{17}$ may be selected from the group consisting of alkyl, cycloalkyl, and fused phenyl-cycloalkyl wherein the point of attachment is on the cycloalkyl wherein the alkyl, cycloalkyl, and fused phenyl-cycloalkyl are optionally substituted with from 1 to three substituents selected from the group consisting of halo, $CF_3$, CN, $OR^{20}$, $SR^{20}$, $S(O)R^{22}$, $SO_2R^{22}$, $SO_2N(R^{20})_2$, $NR^{20}CO_2R^{22}$, $C_{1-2}$ alkyl, and aryl wherein the optional aryl substituent is optionally substituted with from 1 to 3 substituents selected from the group consisting of halo, phenyl, $CF_3$, CN, $OR^{20}$, and $C_{1-6}$ alkyl. In certain preferred compounds of this invention, $R^{17}$ is selected from the group consisting of alkyl, cycloalkyl, and fused phenylcycloalkyl wherein the point of attachment is on the cycloalkyl wherein the alkyl, cycloalkyl, and fused phenylcycloalkyl are optionally substituted with from 1 to two substituents selected from the group consisting of halo, $CF_3$, CN, $OR^{20}$, $SR^{20}$, $S(O)R^{22}$, $SO_2R^{22}$, $C_{1-2}$ alkyl, and aryl wherein the optional aryl substituent is optionally substituted with from 1 to 3 substituents selected from the group consisting of halo, phenyl, $CF_3$, CN, $OR^{20}$, and $C_{1-6}$ alkyl. In other preferred compounds of this invention, $R^{17}$ is selected from the group consisting of alkyl, cycloalkyl, and fused phenylcycloalkyl wherein the point of attachment is on the cycloalkyl wherein the alkyl, cycloalkyl, and fused phenylcycloalkyl are optionally substituted with from 1 to two substituents selected from the group consisting of halo, $CF_3$, $OR^{20}$, and aryl wherein the optional aryl substituent is optionally substituted with from 1 to 3 substituents selected from the group consisting of halo, phenyl, $CF_3$, CN, $OR^{20}$, and $C_{1-6}$ alkyl. Is other preferred compounds of this invention, $R^{17}$ is selected from the group consisting of alkyl having from 1 to 6 carbon atoms, cycloalkyl having from 4 to 6 carbon atoms, fused phenylcycloalkyl with a phenyl that is optionally substituted with from 1 to 2 substituents selected from the group consisting of halo, $CF_3$, OH, methyl, and aryl, and aryl that is optionally substituted with from 1 to 2 substituents selected from the group consisting of halo, $CF_3$, OH, $C_{1-2}$ alkyl, and aryl. In still other preferred compounds of this invention, $R^{17}$ is alkyl having from 1 to 6 carbon atoms and cycloalkyl or $R^{17}$ is a fused phenylcycloalkyl that is optionally substituted with from 1 to 2 substituents selected from the group consisting of halo, $CF_3$, $OR^{20}$, $C_{1-2}$ alkyl, and aryl or $R^{17}$ is phenylmethyl that is optionally substituted with from 1 to 2 substituents selected from the group consisting of halo, $CF_3$, $OR^{20}$, $C_{1-4}$ alkyl, and aryl.

In the compounds of this invention, $R^{20}$ is selected from the group consisting of H, $C_{1-3}$ alkyl, or aryl, wherein the alkyl and aryl substituents are optionally substituted with 1 substituent individually selected from the group consisting of halo, —OMe, and $CF_3$. More preferably, $R^{20}$ is selected from the group consisting of H or $C_{1-3}$ alkyl and most preferably, $R^{20}$ is methyl or H.

Most preferably, the substituted piperazine compounds of this invention are selected from the group consisting of 2-({2-[4-(3-isopropoxy-2-hydroxypropyl)piperazinyl]-N-({2,6-dimethylphenyl)acetamide; N-(2,6-dimethylphenyl)-2-[4-(2-hydroxy-3-indan-2-yloxypropyl)piperazinyl]acetamide; N-(2,6-dimethylphenyl)-2-{4-[2-hydroxy-3-(phenylmethoxy)propyl]piperazinyl}acetamide, 2-[4-(3-{[4-(tert-butyl)phenyl]methoxy}-2-hydroxypropyl)piperazinyl]-N-(2,6-dimethylphenyl)acetamide, N-(2,6-dimethylphenyl)-2-(4-{3-[(2-fluorophenyl)methoxy]-2-hydroxypropyl}piperazinyl)acetamide, 2-(4-{3-[(2,4-difluorophenyl)methoxy]-2-hydroxypropyl}piperazinyl)-N-(2,6-dimethylphenyl)acetamide, N-(2,6-dimethylphenyl)-2-[4-(2-hydroxy-3-{[4-(trifluoromethyl)phenyl]methoxy}propyl)piperazinyl]acetamide, N-(2,6-dimethylphenyl)-2-(4-{2-hydroxy-3-[(2-methoxyphenyl)methoxy]propyl}piperazinyl)acetamide, 2-(4-{3-[(2,4-dimethoxyphenyl)methoxy]-2-hydroxypropyl}piperazinyl)-N-(2,6-dimethylphenyl)acetamide, N-(2,6-dimethylphenyl)-2-(4-{2-hydroxy-3-[(4-methoxyphenyl)methoxy]propyl}piperazinyl)acetamide, N-(2,6-dimethylphenyl)-2-(4-{3-[(4-fluorophenyl)methoxy]-2-hydroxypropyl}piperazinyl)acetamide, N-(2,6-dimethylphenyl)-2-(4-{2-hydroxy-3-[(4-methylphenyl)methoxy]propyl}piperazinyl)acetamide, N-(2,6-dimethylphenyl)-2-(4-{2-hydroxy-3-[(4-phenylphenyl)methoxy]propyl}piperazinyl)acetamide, N-(2,6-dimethylphenyl)-2-(4-{3-[(4-butylphenyl)methoxy]-2-hydroxypropyl}piperazinyl)acetamide, N-(2,6-dimethylphenyl)-2-{4-[2-hydoxy-3-(2-naphthylmethoxy)propyl]piperazinyl}acetamide, N-(2,6-dimethylphenyl)-2-{4-[3-(cyclohexylmethoxy)-2-hydroxypropyl]piperazinyl}acetamide, and N-(2,6-dimethylphenyl)-2-(4-{3-[(4-fluorophenyl)methoxy]-2-hydroxypropyl}-3,3-dimethylpiperazinyl)acetamide.

The following definitions apply to terms as used herein.

"Halo" or "Halogen"—alone or in combination means all halogens, that is, chloro (Cl), fluoro (F), bromo (Br), iodo (I).

"Hydroxyl" refers to the group —OH.

"Thiol" or "mercapto" refers to the group —SH.

"Alkyl"—alone or in combination means an alkane-derived radical containing from 1 to 20, preferably 1 to 15, carbon atoms (unless specifically defined). It is a straight chain alkyl, branched alkyl or cycloalkyl. Preferably, straight or branched alkyl groups containing from 1–15, more preferably 1 to 8, even more preferably 1–6, yet more preferably 1–4 and most preferably 1–2, carbon atoms, such as methyl, ethyl, propyl, isopropyl, butyl, t-butyl and the like. The term "lower alkyl" is used herein to describe the straight chain alkyl groups described immediately above. Preferably, cycloalkyl groups are monocyclic, bicyclic or tricyclic ring systems of 3–8, more preferably 3–6, ring members per ring, such as cyclopropyl, cyclobutyl, cyclopentyl, cyclohexyl, adamantyl and the like. Alkyl also includes a straight chain or branched alkyl group that contains or is interrupted by a cycloalkyl portion. The straight chain or branched alkyl group is attached at any available point to produce a stable compound. Examples of this include, but are not limited to, 4-(isopropyl)- cyclohexylethyl or 2-methyl-cyclopropylpentyl. A substituted alkyl is a straight chain alkyl, branched alkyl, or cycloalkyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Alkenyl"—alone or in combination means a straight, branched, or cyclic hydrocarbon containing 2–20, preferably 2–17, more preferably 2–10, even more preferably 2–8, most preferably 2 to 4 carbon atoms with at least one, preferably 1–3, more preferably 1–2, and most preferably one, carbon to carbon double bond. In the case of a cycloalkyl group, conjugation of more than one carbon to carbon double bond is not such as to confer aromaticity to the ring. Carbon to carbon double bonds may be either contained within a cycloalkyl portion, with the exception of cyclopropyl, or within a straight chain or branched portion. Examples of alkenyl groups include ethenyl, propenyl, isopropenyl, butenyl, cyclohexenyl, cyclohexenylalkyl and the like. A substituted alkenyl is the straight chain alkenyl, branched alkenyl or cycloalkenyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxy, alkoxycarbonyl, aryloxycarbonyl, heteroaryloxycarbonyl, or the like attached at any available point to produce a stable compound.

"Alkynyl"—alone or in combination means a straight or branched hydrocarbon containing 2–20, preferably 2–17, more preferably 2–10, even more preferably 2–8, most preferably 2–4, carbon atoms containing at least one, preferably one, carbon to carbon triple bond. Examples of alkynyl groups include ethynyl, propynyl, butynyl and the like. A substituted alkynyl refers to the straight chain alkynyl or branched alkynyl defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like attached at any available point to produce a stable compound.

"Alkyl alkenyl" refers to a group —R—CR'=CR"R"', where R is lower alkyl, or substituted lower alkyl, R', R"', R"" may independently be hydrogen, halogen, lower alkyl, substituted lower alkyl, acyl, aryl, substituted aryl, hetaryl, or substituted hetaryl as defined below.

"Alkyl alkynyl" refers to a groups —RC?CR' where R is lower alkyl or substituted lower alkyl, R' is hydrogen, lower alkyl, substituted lower alkyl, acyl, aryl, substituted aryl, hetaryl, or substituted hetaryl as defined below.

"Alkoxy" denotes the group —OR, where R is lower alkyl, substituted lower alkyl, acyl, aryl, substituted aryl, aralkyl, substituted aralkyl, heteroalkyl, heteroarylalkyl, cycloalkyl, substituted cycloalkyl, cycloheteroalkyl, or substituted cycloheteroalkyl as defined.

"Alkylthio" denotes the group —SR, —S(O)$_{n=1-2}$—R, where R is lower alkyl, substituted lower alkyl, aryl, substituted aryl, aralkyl or substituted aralkyl as defined herein.

"Acyl" denotes groups —C(O)R, where R is hydrogen, lower alkyl substituted lower alkyl, aryl, substituted aryl and the like as defined herein.

"Aryloxy" denotes groups —OAr, where Ar is an aryl, substituted aryl, heteroaryl, or substituted heteroaryl group as defined herein.

"Amino" denotes the group NRR', where R and R' may independently by hydrogen, lower alkyl, substituted lower alkyl, aryl, substituted aryl, hetaryl, or substituted hetaryl as defined herein or acyl.

"Amido" denotes the group —C(O)NRR', where R and R' may independently by hydrogen, lower alkyl, substituted lower alkyl, aryl, substituted aryl, hetaryl, substituted hetaryl as defined herein.

"Carboxyl" denotes the group —C(O)OR, where R is hydrogen, lower alkyl, substituted lower alkyl, aryl, substituted aryl, hetaryl, and substituted hetaryl as defined herein.

"Aryl"—alone or in combination means phenyl or naphthyl optionally carbocyclic fused with a cycloalkyl of preferably 5–7, more preferably 5–6, ring members and/or optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Substituted aryl" refers to aryl optionally substituted with one or more functional groups, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heterocycle" refers to a saturated, unsaturated, or aromatic carbocyclic group having a single ring (e.g., morpholino, pyridyl or furyl) or multiple condensed rings (e.g., naphthpyridyl, quinoxalyl, quinolinyl, indolizinyl or benzo[b]thienyl) and having at least one hetero atom, such as N, O or S, within the ring, which can optionally be unsubstituted or substituted with, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heteroaryl"—alone or in combination means a monocyclic aromatic ring structure containing 5 or 6 ring atoms, or a bicyclic aromatic group having 8 to 10 atoms, containing one or more, preferably 1–4, more preferably 1–3, even more preferably 1–2, heteroatoms independently selected from the group O, S, and N, and optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable aromatic ring is retained. Examples of heteroaryl groups are pyridinyl, pyridazinyl, pyrazinyl, quinazolinyl, purinyl, quinolinyl, isoquinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, indolyl, benzothiazolyl, benzoxazolyl, and the like. A substituted heteroaryl contains a substituent attached at an available carbon or nitrogen to produce a stable compound.

"Heterocyclyl"—alone or in combination means a non-aromatic cycloalkyl group having from 5 to 10 atoms in which from 1 to 3 carbon atoms in the ring are replaced by heteroatoms of O, S or N, and are optionally benzo fused or fused heteroaryl of 5–6 ring members and/or are optionally substituted as in the case of cycloalkyl. Heterocycyl is also intended to include oxidized S or N, such as sulfinyl, sulfonyl and N-oxide of a tertiary ring nitrogen. The point of attachment is at a carbon or nitrogen atom. Examples of heterocyclyl groups are tetrahydrofuranyl, dihydropyridinyl, piperidinyl, pyrrolidinyl, piperazinyl, dihydrobenzofuryl, dihydroindolyl, and the like. A substituted hetercyclyl contains a substituent nitrogen attached at an available carbon or nitrogen to produce a stable compound.

"Substituted heteroaryl" refers to a heterocycle optionally mono or poly substituted with one or more functional groups, e.g., halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Aralkyl" refers to the group —R—Ar where Ar is an aryl group and R is lower alkyl or substituted lower alkyl group. Aryl groups can optionally be unsubstituted or substituted with, e.g., halogen, lower alkyl, alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Heteroarylalkyl" refers to the group —R—HetAr where HetAr is an heteroaryl group and R lower alkyl or substituted lower alkyl. Heteroarylalkyl groups can optionally be unsubstituted or substituted with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloalkyl" refers to a divalent cyclic or polycyclic alkyl group containing 3 to 15 carbon atoms.

"Substituted cycloalkyl" refers to a cycloalkyl group comprising one or more substituents with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Alkyl cycloalkyl" denotes the group —R-cycloalkyl where cycloalkyl is a cycloalkyl group and R is a lower alkyl or substituted lower alkyl. Cycloalkyl groups can optionally be unsubstituted or substituted with e.g. halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Optional" and "optionally" mean that the subsequently described event or circumstance may or may not occur, and that the description includes instances where the event or circumstance occurs and instances in which it does not. For example, "optional pharmaceutical excipients" indicates that a formulation so described may or may not include pharmaceutical excipients other than those specifically stated to be present, and that the formulation so described includes instances in which the optional excipients are present and instances in which they are not.

"Treating" and "treatment" refer to any treatment of a disease in a mammal, particularly a human, and include:

(i) preventing the disease from occurring in a subject which may be predisposed to the disease but has not yet been diagnosed as having it;

(ii) inhibiting the disease, i.e., arresting its development; or (iii) relieving the disease, i.e., causing regression of the disease.

The compositions of this invention are useful for treating mammals in a therapy selected from the group consisting of protecting skeletal muscles against damage resulting from trauma, protecting skeletal muscles subsequent to muscle or systemic diseases such as intermittent claudication, to treat shock conditions, to preserve donor tissue and organs used in transplants, and to treat cardiovascular diseases including atrial and ventricular arrhythmias, Prinzmetal's (variant) angina, stable angina, and exercise induced angina, congestive heart disease, and myocardial infarction. The treatment is accomplished using a therapeutically effective amount of at least one compound of this invention and/or a pharmaceutically acceptable acid addition salt thereof in admixture with a pharmaceutically acceptable excipient.

Compounds falling within the scope of this invention include the optical isomers (+) and (−) and R- and S- isomers of the above-identified compounds and mixtures thereof. This invention includes the individual isomers and all possible mixtures thereof. All of the aforementioned embodiments include the pharmaceutically acceptable acid addition salts thereof, particularly the mono- and dihydrochlorides, and mixtures thereof.

The compounds having the general formula I can be prepared as outlined in Schemes 1–6. A general synthesis of the compounds of this invention is outlined in Scheme 1.

SCHEME 1

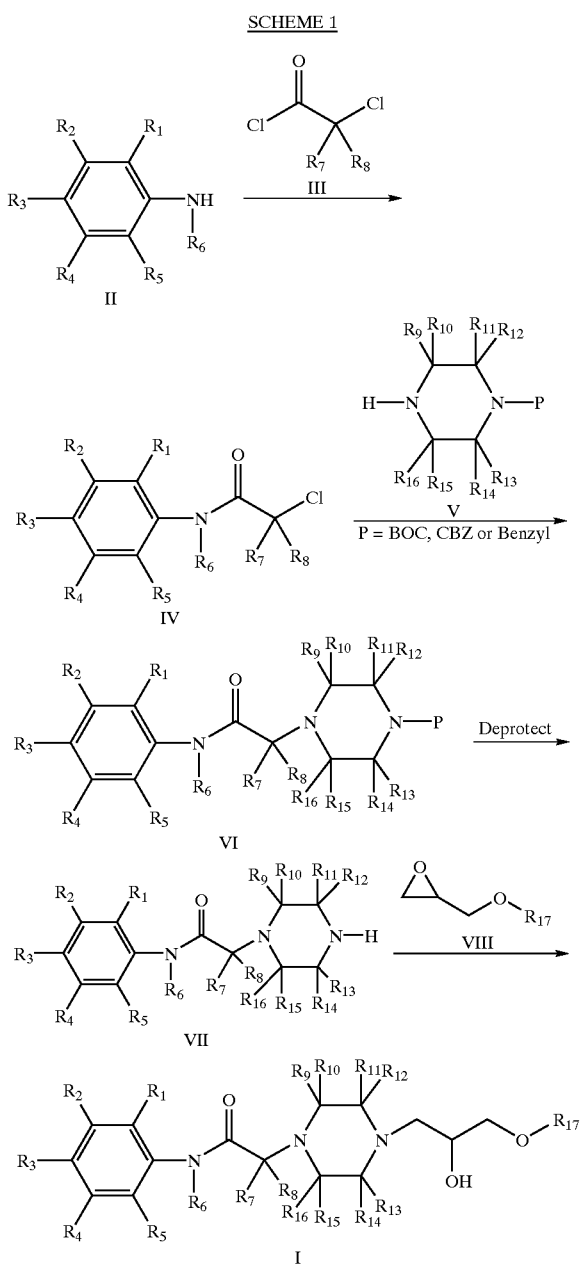

Compound IV can be prepared by N-acylation of substituted aniline II with 2-substituted chloroacetylchloride III. Compound II is available commercially or readily prepared through reduction of the corresponding nitrobenzene derivative (acid/$SnCl_2$ or catalytic hydrogenation, see Advanced Organic Chemistry, Ed. J. March, (1992) A. Wiley-Interscience). Some examples of commercially available substituted aniline II include 2,6-dimethylaniline, 2,3-dimethylaniline, 2-methylaniline 4-methylaniline, 4-methylaniline, 2,4-dichloroaniline, 3,4-dichloroaniline, 2,5-dichloroaniline, 2,4-dichloroaniline, 2-chloroaniline, 3-chloroaniline, 2,6-difluoroaniline, 2,5-difluoroaniline, 3,4-difluoroaniline, 2-fluoroaniline, 4-fluoroaniline, 3-fluoroaniline, 2-fluoro-6-chloroaniline, 4-fluoro-3-chloroaniline.

Compound VI can be obtained by reacting compound IV with N-protected substituted piperazine V through warming in an appropriate solvent (e.g. DMF, EtOH). Protection of the nitrogen of compound V is only required when it is useful to control the regiochemistry of the addition of Compound V with compound IV. In some cases, compound V can be obtained from commercial sources. Examples of commercially available compound corresponding to the general structure V include 2-methyl piperazine, 2,5-dimethyl piperazine, 2,6-dimethyl piperazine and 4-benzyloxycarbonylpiperazin-2-one. Deprotection of compound VI can be accomplished using the standard conditions (e.g. for Boc group use TFA, for CBZ and benzyl use hydrogenation). Compound I can be prepared by reacting compound VII with epoxide VIII through warming in an appropriate solvent (ethanol, DMF).

SCHEME 2

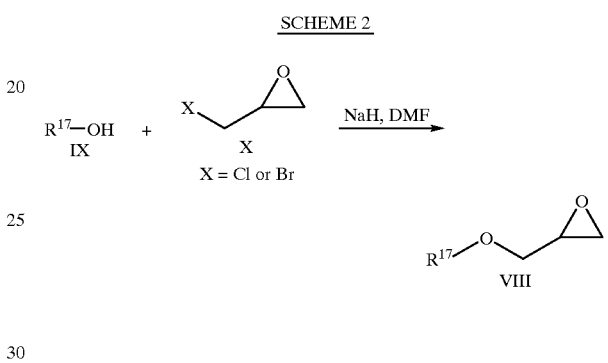

Epoxide VIII can be prepared as outlined in Scheme 2. Heating alkyl alcohol IX with epichlorohydrin or epibromohydrin and sodium hydride in DMF can afford epoxide VIII. In some cases compound VIII can be obtained from commercial resources. Examples of commercially available compounds of general structure VIII include glycidyl isopropyl ether, N butyl glycidyl ether, T butyl glycidyl ether and iso-butyl glycidyl ether.

Compound V can be prepared as described in Scheme 3. Alkylation of compound XII with alkyl halides using t-BuLi as base can afford compound XIII as described by Pohlman et. al. (J. Org. Chem, (1997), 62, 1016–1022). Reduction of XIV using diborane can afford N-benzyl protected version of compound V after N-Boc deprotection with trifluoroacetic acid (TFA, for the diborane reduction see Jacobson et. al, J. Med. Chem, (1999), 42, 1123–1144).

SCHEME 3

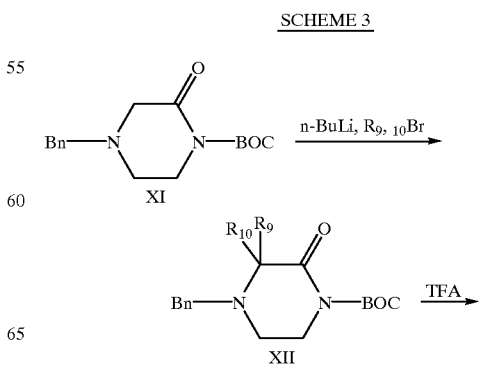

-continued

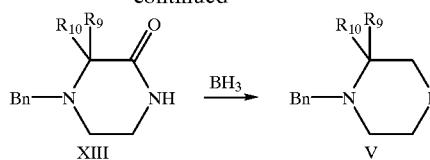

XIII

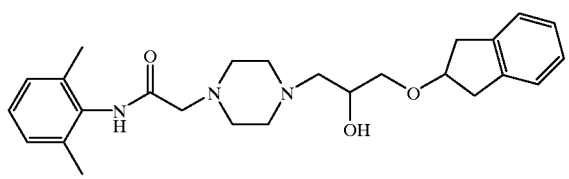

Compound V can also be prepared through standard coupling (eg. EDC or PyBroP) of D or L amino acids as outlined in Scheme 4 [For preparations of diketopiperazines see—P. Cledera et al. Tetrahedron, (1998) p. 12349–12360 and R. A. Smith et al Bioorg. Med. Chem. Lett. (1998) p. 2369–2374]. Reduction of the diketopiperazine with diborane can afford the N-benzyl protected version of compound V.

SCHEME 4

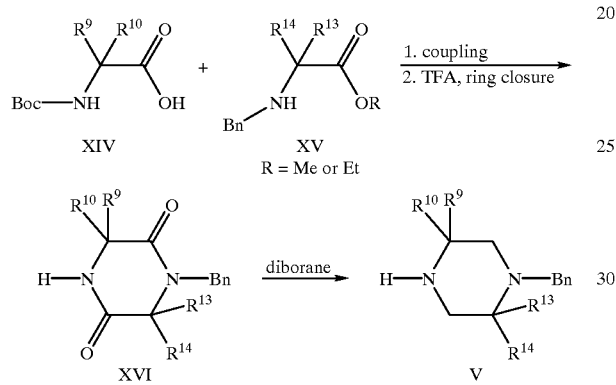

A specific example of the preparation of a compound from this invention is disclosed in Schemes 5 and 6 to further illustrate how to prepare the compounds of this invention.

SCHEME 5

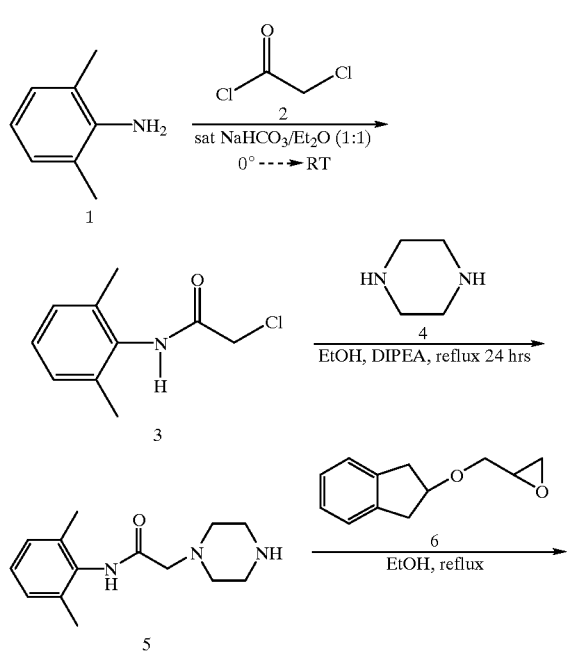

In particular, 2,6-dichloroaniline was acylated with 2-chloroacetyl chloride 2 using saturated bicarbonate and ether (1:1) as base and co-solvent, receptively to afford the chloroacetamide derivative 3. Further reaction of compound 3 with piperazine afforded compound 5 through warming in ethanol. Reaction of compound 5 with epoxide 6 by warming both components in ethanol at reflux afforded piperazine derivative 7. Compound 6 in turn was prepared by warming epibromohydrin with 2-indanol in DMF in presence of NaH as described in Scheme 6.

SCHEME 6

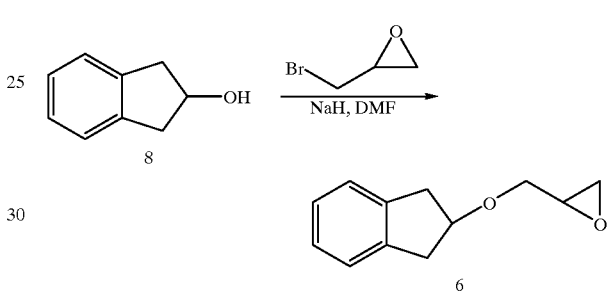

The acid addition salts of the compounds of this invention may be converted to the corresponding free base by treating with a suitable base, such as potassium carbonate or sodium hydroxide, typically in the presence of aqueous solvent, and at a temperature of between about 0 degrees C. and 100 degrees C. The free base form is isolated by conventional means, such as extraction with an organic solvent.

Salts of the compounds of this invention may be interchanged by taking advantage of differential solubilities and volatilities, or by treating with the appropriately loaded ion exchange resin. This conversion is carried out at a temperature between about 0° C. and the boiling point of the solvent being used as the medium for the procedure. Administration of the active compounds and salts described herein can be via any of the accepted modes of administration for therapeutic agents. These methods include oral, parenteral, transdermal, subcutaneous and other systemic modes. The preferred method of administration is oral, except in those cases where the subject is unable to ingest, by himself, any medication. In those instances it may be necessary to administer the composition parentarally.

Depending on the intended mode, the compositions may be in the form of solid, semi-solid or liquid dosage forms, such as, for example, tablets, suppositories, pills, capsules, powders, liquids, suspensions, or the like, preferably in unit dosage forms suitable for single administration of precise dosages. The compositions may include one or more conventional pharmaceutical excipients and at least one active compound of this invention or the pharmaceutically acceptable salts thereof and, in addition, may include other medicinal agents, pharmaceutical agents, carriers, adjuvants, diluents, etc.

The amount of active compound administered will, of course, be dependent on the subject being treated, the subject's weight, the severity of the affliction, the manner of administration and the judgment of the prescribing physician. However, an effective dosage is in the range of 0.1–30 mg/kg/day, preferably 0.5–20 mg/kg/day. For an average 70 kg human, this would amount to 7–2100 mg per day, or preferably 35–1400 mg/day. Since many of the effects of the compounds herein (protect skeletal muscles against damage resulting from trauma; protect skeletal muscles subsequent to muscle or systemic diseases such as intermittent claudication; treat shock conditions; preserve donor tissue and organs used in transplants; and treat cardiovascular diseases including atrial and ventricular arrhythmias, Prinzmetal's (variant) angina, stable angina, exercise induced angina, congestive heart disease, and myocardial infarction) are achieved through a similar mechanism (partial fatty acid oxidation inhibition) dosages (and forms of administration) are all generally within the same general and preferred ranges for all these utilities.

For solid compositions, conventional non-toxic solid include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administrable compositions can, for example, be prepared by dissolving, dispersing, etc. an active compound as defined above and optional pharmaceutical adjuvants in a excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound(s), a therapeutically effective amount, i.e. in an amount effective to alleviate the symptoms of the subject being treated. For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 10%-95% active ingredient, preferably 1–70%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795, which is incorporated herein by reference. In another recent approach, the compositions of this invention can be administered orally in a sustained release dosage form using the compositions and/or methods disclosed in U.S. patent application Ser. No. 09/321,522, filed on May 27, 1999, the specification of which is incorporated herein by reference.

It is within the scope of this invention to administer one or more compounds of this invention to a mammal, and preferably to a human by other known routes of pharmaceutical dosage form administration including, but not limited to by bolus, intravenously, transdermally, through inhalation, sub-cutaneously, or any other therapeutic agent administration method or route know to one skilled in the art.

The following Examples are representative of the invention, but are not to be construed as limiting the scope of the claims.

EXAMPLE 1

N-(2,6-dimethylphenyl)-2-[4-(2-hydroxy-3-indan-2-yloxypropyl)piperazinyl]acetamide (7)

Part A

Synthesis of N-(2,6-dimethylphenyl)-2-chloroacetamide (3)

2,6-dimethylaniline (9.8 g, 81.2 mmol) was dissolved in ether (100 mL) and saturated aqueous $NaHCO_3$ (100 mL) and the reaction mixture was cooled in an ice/water bath. To the cold solution was added chloroacetyl chloride 2 (9.17 g, 81.2 mmol) dropwise over a period of 2 h. The mixture was allowed to warm to RT over 14 h. The mixture was diluted with 100 mL ether and the organic layer was dried over $MgSO_4$, filtered and concentrated to afford compound 3 as a white solid.

Part B

Synthesis of N-(2,6-dimethylphenyl)-2-piperazinylacetamide (5)

To a solution of compound 3 in 100 mL EtOH (5 g, 25.2 mmol) was added compound 4 (2.1 g, 25.0 mmol) and N,N-diisopropylethylamine (3.2 g, 25.2 mmol). The reaction mixture was refluxed for 24 h. The mixture was concentrated in vacuo and the residue was purified by column chromatography (10:1, DCM:MeOH) to afford compound 5.

Part C

Synthesis of 2-(oxiran-2-ylmethoxy)indane (6)

To a solution of 60% NaH (0.18 g, 4.5 mmol) in DMF (10 ml) cooled to 0 degrees was added 2-indanol (0.5 g, 3,73 mmol) in DMF (2 ml) dropwise. After stirring for 30 minutes epibromohydrin (1.11 g, 8.18 mmol) in DMF (1 ml) was added dropwise. The reaction was allowed to warm to room temperature and stirred for 48 h. The solvent was removed in vacuo and the residue was purified using Prep TLC (30:1, DCM:MeOH) to afford compound 6.

Part D

Synthesis of N-(2,6-dimethylphenyl)-2-[4-(2-hydroxy-3-indan-2-yloxypropyl)piperazinyl] acetamide (7)

To a solution of 6 (0.43 g, 2.3 mmol) in ethanol(4 ml) was added 5 (0.405 g, 1.64 mmol). The solution was heated to reflux and stirred for 24 h. Upon completion the solution was concentrated in vacuo and purified using Prep TLC (10:1, DCM:MeOH) to yield 7. Mass Spectrum (M+1)=438.36.

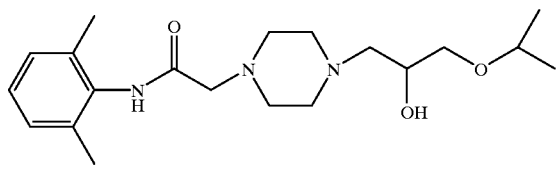

2-({2-[4-(3-isopropoxy-2-hydroxypropyl) piperazinyl]-N-({2,6-dimethylphenyl)acetamide (10)

Compound 10 was prepared in a similar manner to compound 7, substituting the commercially available glycidyl isopropyl ether for 2-(oxiran-2-ylmethoxy)indane in part D to afford 10: Mass spectrum MS (MH+)=364.37.

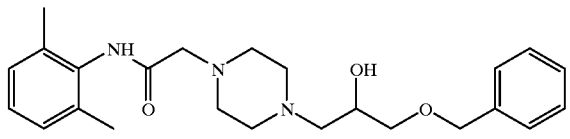

N-(2,6-dimethylphenyl)-2-{4-[2-hydroxy-3 (phenylmethoxy)propyl]piperazinyl}acetamide (11)

Compound 11 was prepared in a similar manner to compound 7, substituting the commercially available benzyl glycidyl ether for 2-(oxiran-2-ylmethoxy)indane in part D to afford 11. Mass Spectrum (M+1)=412.36.

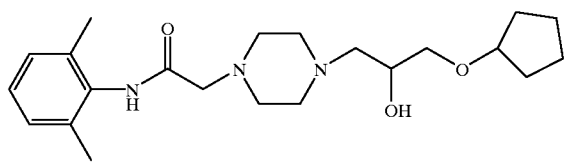

2-({2-[4-(3-cyclopentyloxy-2-hydroxypropyl) piperazinyl]-N-({2,6-dimethylphenyl)acetamide (12)

Compound 12 was prepared in a similar manner to compound 7, substituting the commercially available cyclopentanol for 2-indanol in part C to afford 12: Mass spectrum MS (MH+)=390.

2-({2-[4-(3-cyclohexyloxy-2-hydroxypropyl) piperazinyl]-N-({2,6-dimethylphenyl)acetamide (13)

Compound 13 was prepared in a similar manner to compound 7, substituting the commercially available cyclohexanol for 2-indanol in part C to afford 13: Mass spectrum MS (MH+)=404.

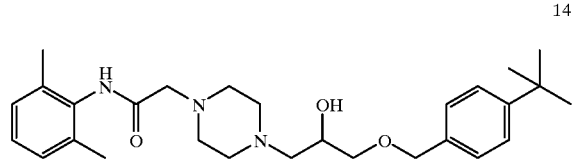

2-[4-(3-{[4-(tert-butyl)phenyl]methoxy}-2-hydroxypropyl)piperazinyl]-N-(2,6-dimethylphenyl) acetamide (14)

Compound 14 was prepared in a similar manner to compound 7, substituting the commercially available 4-t-bu-benzylalcohol for 2-propanol in part C. MS (M+1)= 468.44

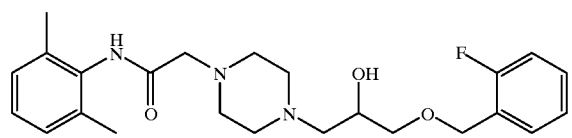

N-(2,6-dimethylphenyl)-2-(4-{3-[(2-fluorophenyl) methoxy]-2-hydroxypropyl}piperazinyl)acetamide (15)

Compound 15 was prepared in a similar manner to compound 7, substituting the commercially available 2-fluorobenzylalcohol for 2-propanol in part C. MS (M+1)= 430.39

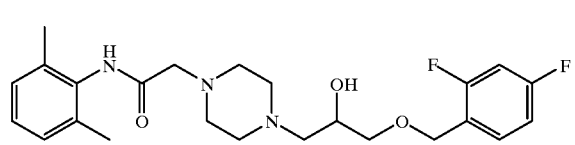

2–4-{-[(2,4-difluorophenyl)methoxy]-2-hydroxypropyl}piperazinyl)-N-(2,6-dimethylphenyl) acetamide(16)

Compound 16 was prepared in a similar manner to compound 7, substituting the commercially available 2,4-difluorobenzylalcohol for 2-propanol in part C. MS (M+1)= 448.38

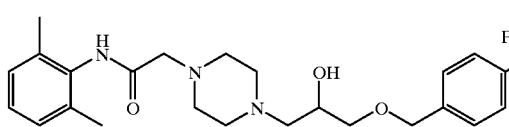

N-(2,6-dimethylphenyl)-2-[4-(2-hydroxy-3-{[4-(trifluoromethyl)phenyl]methoxy}propyl)piperazinyl]acetamide (17)

Compound 17 was prepared in a similar manner to compound 7, substituting the commercially available 4-trifluoromethyl-benzylalcohol for 2-propanol in part C. MS (M+1)=480.37

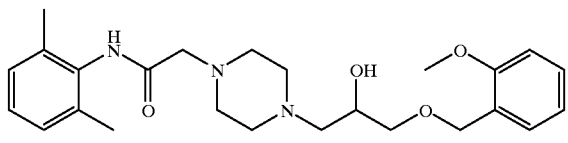

N-(2,6-dimethylphenyl)-2-(4-{2-hydroxy-3-[(2-methoxyphenyl)methoxy]propyl}piperazinyl)acetamide (18)

Compound 18 was prepared in a similar manner to compound 7, substituting the commercially available 2-methoxy-benzylalcohol for 2-propanol in part C. MS (M+1)=442.41

2-(4-{3-[(2,4-dimethoxyphenyl)methoxy]-2-hydroxypropyl}piperazinyl)-N-(2,6-dimethylphenyl)acetamide (19)

Compound 19 was prepared in a similar manner to compound 7, substituting the commercially available 2,4-dimethoxy-benzylalcohol for 2-propanol in part C. MS (M+1)=472.42

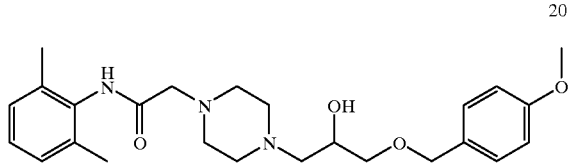

N-(2,6-dimethylphenyl)-2-(4-{2-hydroxy-3-[(4-methoxyphenyl)methoxy]propyl}piperazinyl)acetamide(20)

Compound 14 was prepared in a similar manner to compound 7, substituting the commercially available 4-methoxy-benzylalcohol for 2-propanol in part C. MS (M+1)=442.42

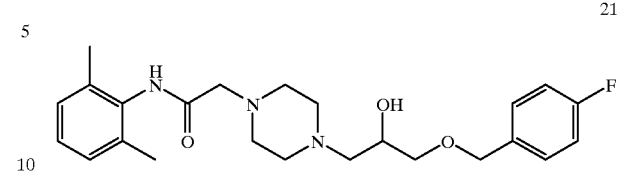

N-(2,6-dimethylphenyl)-2-(4-{3-[(4-fluorophenyl)methoxy]-2-hydroxypropyl}piperazinyl)acetamide (21)

Compound 21 was prepared in a similar manner to compound 7, substituting the commercially available 4-fluoro-benzylalcohol for 2-propanol in part C. MS (M+1)=430.40

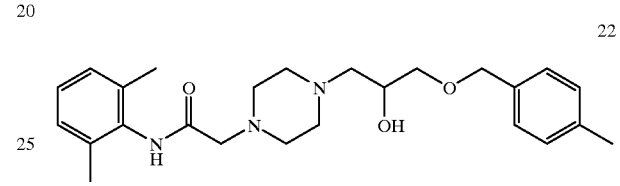

N-(2,6-dimethylphenyl)-2-(4-{2-hydroxy-3-[(4-methylphenyl)methoxy]propyl}piperazinyl)acetamide (22)

Compound 22 was prepared in a similar manner to compound 7, substituting the commercially available 4-methyl-benzylalcohol for 2-propanol in part C. MS (M+1)=426.41

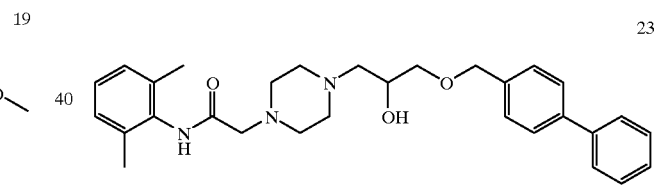

N-(2,6-dimethylphenyl)-2-(4-{2-hydroxy-3-[(4-phenylphenyl)methoxy]propyl}piperazinyl)acetamide (23)

Compound 23 was prepared in a similar manner to compound 7, substituting the commercially available 4-phenylbenzylalcohol for 2-propanol in part C. MS (M+1)=488.42

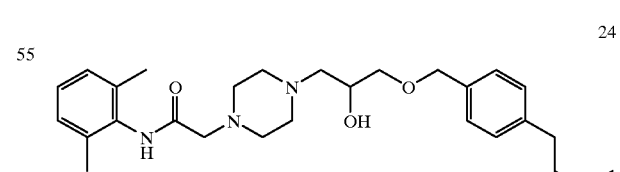

N-(2,6-dimethylphenyl)-2-(4-{3-[(4-butylphenyl)methoxy]-2-hydroxypropyl}piperazinyl)acetamide (24)

Compound 24 was prepared in a similar manner to compound 7, substituting the commercially available 4-n- bu-benzylalcohol for 2-propanol in part C. MS (M+1)= 468.45

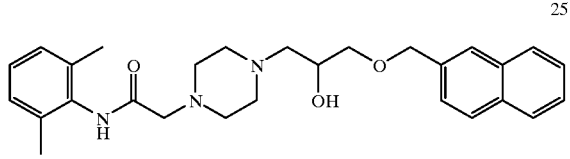

N-(2,6-dimethylphenyl)-2-{4-[2-hydroxy-3-(2-naphthylmethoxy)propyl]piperazinyl}acetamide (25)

Compound 25 was prepared in a similar manner to compound 7, substituting the commercially available 2-naphthylmethanol for 2-propanol in part C. MS (M+1)= 462.41

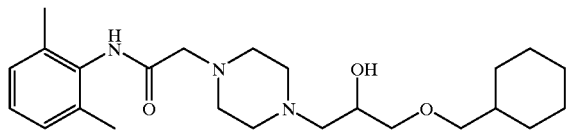

N-(2,6-dimethylphenyl)-2-{4-[3-(cyclohexylmethoxy)-2-hydroxypropyl]piperazinylacetamide (26)

Compound 26 was prepared in a similar manner to compound 7, substituting the commercially available cyclohexylmethanol for 2-propanol in part C. MS (M+1)=418.55

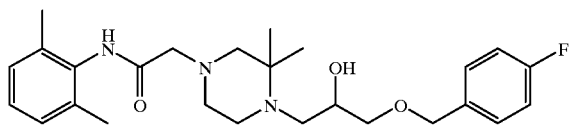

N-(2,6-dimethylphenyl)-2-(4-{3-[(4-fluorophenyl)methoxy]-2-hydroxypropyl}-3,3-dimethylpiperazinyl)acetamide (27)

Compound 26 was prepared in a similar manner to compound 7, substituting the commercially available 4-fluorobenzylalcohol for 2-propanol in part C and 2,2-dimethylpiperazine for compound 4 part B. MS (M+1)= 458.5

EXAMPLE 2

Mitochondrial Assays

Rat heart mitochodria were isolated by the method of Nedergard and Cannon (Methods in Enzymol. 55, 3, 1979).

Palmitoyl CoA oxidation—The Palmityl CoA oxidation was carried out in a total volume of 100 microliters containing the following agents: 110 mM KCl, 33 mM Tris buffer at pH 8, 2 mM KPi, 2 mM $MgCl_2$, 0.1 mM EDTA, 14.7 microM defatted BSA, 0.5 mM malic acid, 13 mM carnitine, 1 mM ADP, 52 micrograms of mitochondrial protein, and 16 microM 1-C14 palmitoyl CoA (Sp. Activity 60 mCi/mmole; 20 microCi/ml, using 5 microliters per assay). The compounds of this invention were added in a DMSO solution at the following concentrations: 100 microM, 30 microM, and 3 microM. In each assay, a DMSO control was used. After 15 min at 30 C, the enzymatic reaction was centrifuged (20,000 g for 1 min), and 70 microliters of the supernatant was added to an activated reverse phase silicic acid column (approximately 0.5 ml of silicic acid). The column was eluted with 2 ml of water, and 0.5 ml of the eluent was used for scintillation counting to determine the amount of $C^{14}$ trapped as $C^{14}$ bicarbonate ion.

TABLE 1

Inhibition of mitochondrial fatty acid oxidation using palmitoyl CoA as substrate - % of Control at 3 concentrations.

| Compound # | 100 $\mu$M | 30 $\mu$M | 3 $\mu$M |
| --- | --- | --- | --- |
| Ranolazine | 75% | 90% | — |
| 10 | 100% | 97% | — |
| 7 | 68% | — | — |
| 11 | 79% | — | — |
| 12 | 41% | — | — |
| 13 | 30% | — | — |
| 14 | 21% | — | — |
| 15 | 100% | — | — |
| 16 | 97% | — | — |
| 17 | 35% | — | — |
| 18 | 96% | — | — |
| 19 | 97% | — | — |
| 20 | 100% | — | — |
| 21 | 87% | — | — |
| 22 | 45% | — | — |
| 23 | 12% | — | — |
| 24 | 15% | — | — |
| 25 | 38% | — | — |
| 26 | 70% | — | — |
| 27 | 73% | — | — |

EXAMPLE 3

Palmitoyl Carnitine Oxidation

The Palmitoyl carnitine oxidation was carried out in a total volume of 100 microliters containing the following agents: 110 mM KCl, 33 mM Tris buffer at pH 8, 2 mM KPi, 2 mM $MgCl_2$, 0.1 mM EDTA, 0.1 mg/ml of defatted BSA, 0.5 mM malic acid, 3 mM ADP, 52 micrograms of mitochondrial protein, and 43 microM 1-C14 palmitoyl carnitine (Sp. Activity 60 mCi/mmole; 20 microCi/ml, using 5 microliters per assay). The compounds of this invention were added in a DMSO solution at the following concentrations: 100 microM, 30 microM, and 3 microM. In each assay, a DMSO control was used. After 15 min at 30° C., the enzymatic reaction was centrifuged (20,000 g for 1 min), and 70 microliters of the supernatant was added to an activated reverse phase silicic acid column (approximately 0.5 ml of silicic acid). The column was eluted with 2 ml of water, and 0.5 ml of the eluent was used for scintillation counting to determine the amount of $C^{14}$ trapped as $C^{14}$ bicarbonate ion. The data are presented as % activity of control.

TABLE 2

Inhibition of mitochondrial fatty acid oxidation using palmitoyl carnitine as substrate - % of Control At 3 concentrations.

| Compound # | 100 µM | 30 µM | 3 µM |
|---|---|---|---|
| Ranolazine | 63% | 98% | — |
| 10 | 80% | — | — |
| 7 | — | — | — |
| 11 | — | — | — |
| 12 | — | — | — |
| 13 | — | — | — |

EXAMPLE 4

Metabolic Stability

As a measure of metabolic stability the compounds of this invention were incubated with human liver S-9 microsomal fractions. After, 30 minutes at 37 C, the amount of parent drug remaining was determined using LC-mass spec. The response factors for each compound was determined by establishing a standard curve and using an internal standard during the analysis of the samples. An average of five experiments for percentage of ranolazine remaining at the 30 minute time point is 57%. The compounds of this invention were assayed as described in the protocol below and the percentage of parent remaining was divided by the average % of ranolazine remaining (57%) affording a metabolic stability factor. A compound with a stability number greater than 1.2 has a better stability than ranolazine in the liver S-9 assay. A compound with a stability number between 1.2 and 0.8 has an equivalent stability in the liver S-9 assay. A compound with a stability number less than 0.8 is less stable than ranolazine in the liver S-9 assay.

The purpose of this experiment is to compare the percentages remaining for compounds of this invention with the percentage remaining for ranolazine after 30 minutes of incubation with human liver S9 fractions.

Reagents

The following reagents were used; Potassium phosphate, 0.5M pH 74. (incubation buffer), kept at room temperature; 0.05M MgCl$_2$ kept at 4° C.; β-Nicotinamide adenine dinucleotide phosphate, tetrasodium salt, reduced form (NADPH), 0.02M solution in water (~16.6 mg/mL) from Sigma Lot #79H7044 prepared on day of use. 1 mM of ranolazine or Compounds 7, 9, and 10–13 in ACN further diluted to obtain 100 µM in 10% ACN; Human S9 stock: 20 mg/mL from Gentest Lot 3.

Procedure

Incubation mixtures were prepared as follows:

TABLE 3

| Component | Volume per 0.25 mL of Incubation Mixture | Final concentration |
|---|---|---|
| 100 µM CVT compounds | 25 µL | 10 µM |
| MgCl$_2$ | 25 µL | 0.005 M |
| NADPH | 25 µL | 0.002 M |
| S9 | 25 µL | 2 mg/mL |
| Incubation Buffer | 25 µL | 0.05 M |
| Water | 125 µL | — |

* 1% organic solvent (acetonitrile) was used in incubation mixture. Generally, 30 incubates were prepared at a time by pre-mixing 0.75 mL of MgCl$_2$, 0.75 mL of incubation buffer, 0.75 mL of NADPH, 3.75 mL of water. Then pipette 200 µL/incubate, add 25 µL of compound being tested, mix, and initiate reaction by addition of S-9.

Combine all components with incubation buffer and re-pipette 200 µL/tube+25 µL of the compound being tested along with 25 µL of S-9.

After 5 min of pre-incubation at 37° C., at 0 and 30 min after starting the reaction, a 50 µl aliquot of the incubation mixture was removed and added to 100 µL of 9:1 acetonitrile: methanol containing the internal standard.

The mixture was centrifuged and a 100 µL aliquot of the supernatant was diluted in 1 mL of solvent C (0.1% Formic Acid in water). Then samples were analyzed for change between the ratio of compound to internal standard at time zero and 30 minutes by LC/MS (injected 10 µL).

Analytical and Data Calculations

Samples were analyzed for the starting compounds and potential metabolite/s by LC/MS using an internal standard on a Micromass platform mass spec with a Keystone Inc. BDS ODS-C18 column with a flow rate of 0.25 ml/min. Following the above procedure resulted in the following relative stability factors as compared to ranolazine for the compounds of this invention as illustrated in Table 4.

TABLE 4

| Compound # | Liver S-9 stability factor |
|---|---|
| Ranolazine | 1.0 |
| 10 | — |
| 7 | 0.37 |
| 11 | — |
| 12 | 1.48 |
| 13 | 1.20 |
| 15 | — |
| 16 | — |
| 17 | 1.0 |
| 18 | — |
| 19 | — |
| 20 | — |
| 21 | — |
| 22 | 0.61 |
| 23 | 0.05 |
| 24 | 0.02 |
| 25 | 0.01 |
| 26 | — |
| 27 | — |

We claim:

1. A substituted piperazine compound having the following formula:

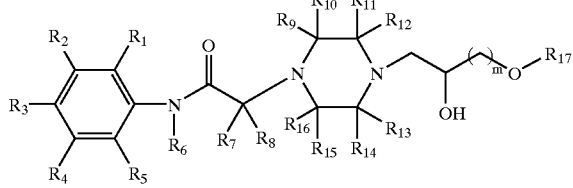

wherein m=1 or 2;

$R^1$, $R^2$, $R^3$, $R^4$ and $R^5$ are each independently selected from the group consisting of hydrogen, halo, $CF_3$, $OR^{22}$ and straight or branched $C_{1-4}$ alkyl that is optionally substituted with $CF_3$ and wherein $R^{22}$ is a straight or branched $C_{1-3}$ alkyl;

$R^6$, $R^7$ and $R^8$ each independently selected from the group consisting of hydrogen and $C_{1-3}$ alkyl;

$R^9$, $R^{10}$, $R^{11}$, $R^{12}$, $R^{13}$, $R^{14}$, $R^{15}$ and $R^{16}$ are each independently selected from the group consisting of hydrogen, $CON(R^{20})_2$, straight or branched $C_{1-4}$ alkyl, or aryl wherein the alkyl and aryl substituents are each optionally substituted with 1 substituent selected from the group consisting of halo, $CF_3$, $OR^{20}$, $N(R^{20})_2$, $CON(R^{20})_2$ or aryl wherein $R^9$ and $R^{10}$ may together form a carbonyl, or $R^{11}$ and $R^{12}$ may together form a carbonyl, or $R^{13}$ and $R^{14}$ may together form a carbonyl, or $R^{15}$ and $R^{16}$ may together form a carbonyl;

$R^{17}$ is selected from the group consisting of straight or branched alkyl, cycloalkyl, and fused phenylcycloalkyl wherein the point of attachment is on the cycloalkyl wherein the alkyl, cycloalkyl, and fused phenylcycloalkyl are optionally substituted with from 1 and two substituents selected from the group consisting of halo, $CF_3$, $OR^{20}$, and aryl wherein the optionally aryl substituent is optionally substituted with from 1 to 3 substituents selected from the group consisting of halo, phenyl, $CF_3$, CN, $OR^{20}$, and straight or branched $C_{1-6}$ alkyl; and $R^{20}$ is selected from the group consisting of H, straight or branched $C_{1-3}$ alkyl, or aryl, wherein the alkyl and aryl substituents are optionally substituted with 1 substituents individually selected from the group consisting of halo, —OMe, and $CF_3$.

2. The compound of claim 1 wherein $R^9$, $R^{10}$, $R^{11}$, $R^{12}$, $R^{13}$, $R^{14}$, $R^{15}$ and $R^{16}$ are each independently selected from the group consisting of hydrogen and $C_{1-4}$ alkyl, or $R^9$ and $R^{10}$ together form a carbonyl, or $R^{11}$ and $R^{12}$ together form a carbonyl, or $R^{13}$ and $R^{14}$ together form a carbonyl, or $R^{15}$ and $R^{16}$ together form a carbonyl, $R^{10}$ and $R^{11}$ together form —$CH_2CH_2CH_2CH_2$—.

3. The compound of claim 1 wherein $R^9$, $R^{10}$, $R^{11}$, $R^{12}$, $R^{13}$, $R^{14}$, $R^{15}$ and $R^{16}$ are each independently selected from the group consisting of hydrogen, $CON(R^{20})_2$, $C_{1-3}$ alkyl, or aryl wherein the alkyl and aryl substituents are optionally substituted with 1 substituent selected from the group consisting of halo, $N(R^{20})_2$, and aryl or wherein $R^9$ and $R^{10}$ may together form a carbonyl, or $R^{11}$ and $R^{12}$ may together form a carbonyl.

4. The compound of claim 1 wherein $R^9$, $R^{10}$, $R^{11}$, $R^{12}$, $R^{13}$, $R^{14}$, $R^{15}$ and $R^{16}$ are each independently selected from the group consisting of hydrogen, or $C_{1-2}$ alkyl, wherein the alkyl substituent is optionally substituted with 1 substituent selected from the group consisting of $N(R^{20})_2$ or aryl or wherein $R^9$ and $R^{10}$ may together form a carbonyl.

5. The compound of claim 1 wherein $R^1$, $R^2$, $R^3$, $R^4$ and $R^5$ are each independently selected from the group consisting of hydrogen, halo, $CF_3$, $OR^{20}$, or $C_{1-3}$ alkyl wherein the alkyl substituent is optionally substituted with $CF_3$.

6. The compound of claim 1 wherein $R^6$, $R^7$ and $R^8$ each independently selected from the group consisting of hydrogen or methyl.

7. The compound of claim 1 wherein m=1;

$R^1$, $R^2$, $R^3$, $R^4$ and $R^5$ are each independently selected from the group consisting of hydrogen, $CF_3$, $OR^{20}$, or $C_{1-2}$ alkyl;

$R^6$, $R^7$ and $R^8$ are each hydrogen;

$R^9$, $R^{10}$, $R^{11}$, $R^{12}$, $R^{13}$, $R^{14}$, $R^{15}$ and $R^{16}$ are each independently selected from the group consisting of hydrogen or $C_{1-2}$ alkyl, or wherein $R^9$ and $R^{10}$ may together form a carbonyl;

$R^{17}$ is selected from the group consisting of alkyl, cycloalkyl, and fused phenylcycloalkyl wherein the point of attachment is on the cycloalkyl wherein the alkyl, cycloalkyl, and fused phenylcycloalkyl are optionally substituted with from 1 to two substituents selected from the group consisting of halo, $CF_3$, $OR^{20}$, and aryl wherein the optional aryl substituents is optionally substituted with from 1 and 2 substituents selected from the group consisting of halo, phenyl, $CF_3$, $OR_{20}$, and $C_{1-4}$ alkyl; and $R^{20}$ is selected from the group consisting of H or $C_{1-3}$ alkyl.

8. The compound of claim 7 wherein $R^{17}$ is selected from the group consisting of alkyl, cycloalkyl, and fused phenylcycloalkyl wherein the point of attachment is on the cycloalkyl wherein the alkyl, cycloalkyl, and fused phenylcycloalkyl are optionally substituted with 1 substituent selected from the group consisting of halo, $CF_3$, $OR^{20}$, and aryl wherein the optional aryl substituent is optionally substituted with from 1 to 2 substituents selected from the group consisting of halo, phenyl, $CF_3$, $OR^{20}$, and $C_{1-4}$ alkyl.

9. The compound of claim 1 wherein $R^{17}$ is selected from the group consisting of alkyl, cycloalkyl, and fused phenylcycloalkyl wherein the point of attachment is on the cycloalkyl wherein the alkyl, cycloalkyl, and fused phenylcycloalkyl are optionally substituted with 1 substituent selected from the group consisting of halo, $CF_3$, $OR^{20}$, and aryl wherein the optional aryl substituent is optionally substituted with from 1 and 2 substituents selected from the group consisting of halo, phenyl, $CF_3$, $OR^{20}$, and $C_{1-4}$ alkyl.

10. The compound of claim 7 wherein $R^1$, $R^2$, $R^3$, $R^4$ and $R^5$ are each independently selected from the group consisting of hydrogen, halo, $CF_3$, $OCH_3$, or methyl.

11. The compound of claim 7 wherein $R^1$, $R^2$, $R^3$, $R^4$ and $R^5$ are each independently selected from the group consisting of hydrogen, or methyl.

12. The compound of claim 7 wherein $R^{11}$ and $R^{15}$ are each selected from the group consisting of hydrogen or methyl, $R^9$, $R^{10}$, $R^{12}$, $R^{13}$, $R^{14}$ and $R^{16}$ are each hydrogen and $R^9$ and $R^{10}$ may together form a carbonyl.

13. A substituted piperazine compound having the following formula:

wherein
m=1;

R$^1$, R$^2$, R$^3$, R$^4$ and R$^5$ are each independently selected from the group consisting of hydrogen, or methyl;

R$^6$, R$^7$ and R$^8$ are each hydrogen;

R$^{11}$ and R$^{15}$ are each selected from the group consisting of hydrogen or methyl, R$^9$, R$^{10}$, R$^{12}$, R$^{13}$, R$^{14}$ and R$^{16}$ are each hydrogen and R$^9$ and R$^{10}$ may together form a carbonyl;

R$^{17}$ is selected from the group consisting of straight or branched alkyl, cycloalkyl, and fused phenylcycloalkyl wherein the point of attachment is on the cycloalkyl wherein the alkyl, cycloalkyl, and fused phenylcycloalkyl are optionally substituted with 1 substituent selected from the group consisting of halo, CF$_3$, OR$^{20}$, and aryl wherein the optional aryl substituent is optionally substituted with from 1 to 2 substituents selected from the group consisting of halo, phenyl, CF$_3$, OR$^{20}$, and straight or branched C$_{1-4}$ alkyl; and R$^{20}$ is methyl or H.

14. The compound of claim 13 wherein R$^{17}$ is alkyl having from 1 to 6 carbon atoms and cycloalkyl.

15. The compound of claim 13 wherein R$^{17}$ is a fused phenylcycloalkyl that is optionally substituted with from 1 to 2 substituents selected from the group consisting of halo, CF$_3$, OR$^{20}$, C$_{1-2}$ alkyl, and aryl.

16. The compound of claim 13 wherein R$^{17}$ is phenylmethyl that is optionally substituted with from 1 to 2 substituents selected from the group consisting of halo, CF$_3$, OR$^{20}$, C$_{1-4}$ alkyl, and aryl.

17. The compound of claim 13 wherein R$^2$, R$^3$, and R$^4$ are each hydrogen and R$^1$ and R$^5$ are each methyl.

18. A substituted piperazine compound having the following formula:

I wherein
m=1;

R$^1$, R$^2$, R$^3$, R$^4$ and R$^5$ are each independently selected from the group consisting of hydrogen or methyl;

R$^6$, R$^7$ and R$^8$ each hydrogen;

R$^9$, R$^{10}$, R$^{11}$, R$^{12}$, R$^{13}$, R$^{14}$, R$^{15}$ and R$^{16}$ are each hydrogen; and R$^{17}$ is selected from the group consisting of straight or branched alkyl having from 1 and 6 carbon atoms, cycloalkyl having from 4 to 6 carbon atoms, fused phenylcycloalkyl that is optionally substituted with from 1 to 2 substituents selected from the group consisting of halo, CF$_3$, OH, methyl, and aryl, and aryl that is optionally substituted with from 1 to 2 substituents selected from the group consisting of halo, CF$_3$, OH, C$_{1-2}$ alkyl, and aryl.

19. The compound of claim 1 selected from the group consisting of substituted piperazine compound selected from the group consisting of 2-({2-[4-(3-isopropoxy-2-hydroxypropyl)piperazinyl]-N-({2,6-dimethylphenyl)acetamide; N-(2,6-dimethylphenyl)-2-[4-(2-hydroxy-3-indan-2-yloxypropyl)piperazinyl]acetamide; N-(2,6-dimethylphenyl)-2-{4-[2-hydroxy-3-(phenylmethoxy)propyl]piperazinyl}acetamide, 2-({2-[4-(3-cyclopentyloxy-2-hydroxypropyl)piperazinyl]-N-({2,6-dimethylphenyl)acetamide, 2-({2-[4-(3-cyclohexyloxy-2-hydroxypropyl)piperazinyl]-N-({2,6-dimethylphenyl)acetamide, 2-[4-(3-{[4-(tert-butyl)phenyl]methoxy}-2-hydroxypropyl)piperazinyl]-N-(2,6-dimethylphenyl)acetamide, N-(2,6-dimethylphenyl)-2-(4-{3-[(2-fluorophenyl)methoxy]-2-hydroxypropyl}piperazinyl)acetamide, 2-(4-{3-[(2,4-difluorophenyl)methoxy]-2-hydroxypropyl}piperazinyl)-N-(2,6-dimethylphenyl)acetamide, N-(2,6-dimethylphenyl)-2-[4-(2-hydroxy-3-{[4-(trifluoromethyl)phenyl]methoxy}propyl)piperazinyl]acetamide, N-(2,6-dimethylphenyl)-2-(4-{2-hydroxy-3-[(2-methoxyphenyl)methoxy]propyl}piperazinyl)acetamide, 2-(4-{3-[(2,4-dimethoxyphenyl)methoxy]-2-hydroxypropyl}piperazinyl)-N-(2,6-dimethylphenyl)acetamide, N-(2,6-dimethylphenyl)-2-(4-{2-hydroxy-3-[(4-methoxyphenyl)methoxy]propyl}piperazinyl)acetamide, N-(2,6-dimethylphenyl)-2-(4-{3-[(4-fluorophenyl)methoxy]-2-hydroxypropyl}piperazinyl)acetamide, N-(2,6-dimethylphenyl)-2-(4-{2-hydroxy-3-[(4-methylphenyl)methoxy]propyl}piperazinyl)acetamide, N-(2,6-dimethylphenyl)-2-(4-{2-hydroxy-3-[(4-phenylphenyl)methoxy]propyl}piperazinyl)acetamide, N-(2,6-dimethylphenyl)-2-(4-{3-[(4-butylphenyl)methoxy]-2-hydroxypropyl}piperazinyl)acetamide, N-(2,6-dimethylphenyl)-2-{4-[2-hydoxy-3-(2-naphthylmethoxy)propyl]piperazinyl}acetamide, N-(2,6-dimethylphenyl)-2-{4-[3-(cyclohexylmethoxy)(-2-hydroxypropyl]piperazinyl}acetamide, and N-(2,6-dimethylphenyl)-2-(4-{3-[(4-fluorophenyl)methoxy]-2-hydroxypropyl}-3,3-dimethylpiperazinyl)acetamide.

20. A method of treatment comprising administering a therapeutically effective amount of a compound of claim 1 to a mammal in need of a treatment selected from the group consisting of protecting skeletal muscles against damage resulting from trauma, protecting skeletal muscles subsequent to muscle or systemic diseases, treating shock conditions, preserving donor tissue and organs used in transplants, or treating cardiovascular diseases.

21. The method of claim 20 wherein the cardiovascular disease is selected from the group consisting of atrial and ventricular arrhythmias, Prinzmetal's (variant) angina, stable angina, exercise induced angina, congestive heart disease, or myocardial infarction.

22. The method of claim 20 wherein the therapeutically effective amount ranges from about 0.01 to about 100 mg/kg weight of the mammal.

23. The method of claim 20 wherein the mammal is a human.

24. A pharmaceutical composition of matter comprising the composition of claim 1 and one or more pharmaceutical excipients.

25. The pharmaceutical composition of matter of claim 24 wherein the pharmaceutical composition is in the form of a solution.

26. The pharmaceutical composition of matter of claim 24 wherein the pharmaceutical composition is in a form selected from the group consisting of a tablet or a capsule.

* * * * *